US006322964B1

(12) United States Patent
Cosand et al.

(10) Patent No.: US 6,322,964 B1
(45) Date of Patent: Nov. 27, 2001

(54) SYNTHETIC HIV-2 GAG AND ENV OLIGOPEPTIDES REACTIVE WITH HIV-2 SPECIFIC ANTIBODIES

(75) Inventors: Wesley L. Cosand, Bothell; Andrew J. Watson, Seattle; Raymond L. Houghton, Kirkland, all of WA (US); Luc Montagnier, LePlessy-Robinson (FR); Marc Alizon; Solange Chamaret, both of Paris (FR)

(73) Assignees: Genetic Systems Corporation, Seattle, WA (US); Institut Pasteur, Paris (FR)

( * ) Notice: Subject to any disclaimer, the term of this patent is extended or adjusted under 35 U.S.C. 154(b) by 0 days.

(21) Appl. No.: 08/268,388

(22) Filed: Jun. 30, 1994

Related U.S. Application Data

(63) Continuation of application No. 08/037,506, filed on Mar. 24, 1993, now abandoned, which is a continuation of application No. 07/807,426, filed on Dec. 13, 1991, now abandoned, which is a continuation of application No. 07/622,299, filed on Dec. 5, 1990, now abandoned, which is a continuation of application No. 07/035,408, filed on Apr. 7, 1987, now abandoned, which is a continuation-in-part of application No. 07/003,764, filed on Jan. 16, 1987, now Pat. No. 5,051,496, and a continuation-in-part of application No. 07/013,477, filed on Feb. 11, 1987, now Pat. No. 5,079,342, and a continuation-in-part of application No. 07/030,403, filed on Mar. 25, 1987, now abandoned.

(51) Int. Cl.[7] .......... C12Q 1/70
(52) U.S. Cl. .......... 435/5; 435/7.1; 530/300; 530/324; 530/325; 530/326; 530/327; 424/188.1
(58) Field of Search .......... 435/5, 7.1; 530/324, 530/326, 327

(56) References Cited

U.S. PATENT DOCUMENTS

| | | | | |
|---|---|---|---|---|
| 4,629,783 | * | 12/1986 | Cosand et al. | 530/324 |
| 5,051,496 | * | 9/1991 | Alizon et al. | 530/324 |
| 5,079,342 | * | 1/1992 | Alizon et al. | 530/324 |

OTHER PUBLICATIONS

Geysen et al., 1988, Cognitive features of continuous antigenic determinants, J. Molec. Recog., 1:32–41.*

Cease and Berzofsky, 1994, Toward a vaccine for AIDS:The emergence of immunobiology–based vaccine development, Annu. Rev. Immunol., 12:923–989.*

Mateu et al., 1989, Implications of a quasispecies genome structure:Effect of frequent, naturally occurring amino acid substitutions on the antigenicity of foot–and–mouth disease virus, Proc. Natl. Acad. Sci. USA, 86:5883–5887.*

Clavel et al., "LAV Type II: A Second Retrovirus Associated Associated With AIDS in West Africa," C. R. Acad Sci. (Paris), 302:485–488 (1986).

Clavel et al., "Isolation of a New Human Retrovirus from West Africa Patients with AIDS", Science 233:343–346 (1986).

Clavel et al., "Molecular Cloning And Polymorphism Of The Human Immune Deficiency Virus Type 2," *Nature* 324:671–695 (1986).

Kanki et al., "New Human T–Lymphotrophic Retrovirus Related To Simian T–Lymphotrophic Virus Type III (STLC–IIIagm)", Science 232:238–243 (1986).

Barin et al., "Serological Evidence For Virus Related to Simian T–Lymphotropic Retrovirus III In Residents Of West Africa", Lancet 2:1384–1389 (1985).

Hopp et al., "Production Of Protein Antigenic Determinants From Amino Acid Sequences", Proc. Nat. Acad. Sci. USA 78:3224–3828 (1981).

Hopp, "A Synthetic Peptide With Hepatitis B. Surface Antigen Reactivity," *Molec. Immunol.* 18:869–872 (1981).

Kazin, et al., "Structurally Inherent Antigenic Sites", Biochem. J. 203:201–208 (1982).

Green et al., "Immunogenic Structure Of the Influenza Virus Hemagglutinin", Cell 28:477–487 (1982).

Tainer et al., "The Reactivity Of Anti–Peptide Antibodies Is a Function Of the Atomic Mobility Of Sites In a Protein," Nature, 314(1984) 127–34.

Wong–Staal et al. NTIS Publication No. PB 86–131562 (U.S. Ser. No. 779,431) Entitled HTLV–III/LAV Synthetic Peptide, Filed Sep. 24, 1985.

Wang et al., "Detection Of Antibodies To Human T–Lymphotropic Virus Type III By Using A Synthetic Peptide Of 21 Amino Acid Residues Corresponding to a Highly Antigenic Segment Of gp41 or Envelope Protein," *Proc. Natl. Acad. Sci. USA.* 83:6159–6163 (1986).

Pauletti et al., "Application Of a Modified Computer Algorithim In Determining Potential Antigenic Determinants Associated With the AIDS Virus Glycoprptein", *Analyt. Biochem.* 151:540–546 (1985).

Starchich et al., "Identification And Characterization Of Onsserved And Variable Regions In The Envelope Gene Of HTLV–III/LAV, The Retrovirus of AIDS", Cell 45:637–648 (1986).

* cited by examiner

*Primary Examiner*—Laurie Scheiner
*Assistant Examiner*—Jeffrey S. Parkin
(74) *Attorney, Agent, or Firm*—Townsend and Townsend and Crew LLP

(57) ABSTRACT

Peptide sequences are disclosed which immunologically mimic proteins encoded by the env and gag regions of LAV-2, a retrovirus associated with AIDS. The peptide can be used in various specific binding assays to detect the presence of antibodies to LAV-2 in individuals previously exposed to the virus. The peptides enable one to distinguish the presence of antibodies to LAV-2 from antibodies to HIV-1.

12 Claims, 2 Drawing Sheets

FIG. 1

```
LAV.2 M----------MNQLLIAILLA--SACLVYCTQYVTVFYGVPTWKNATIPLFCATRNR--DT-----WGTIQCLPDNDDYQEIT-LNVTEAFDAWNNTV  79
      *                 **     *          *** **** ** **  ****       **     * * * *      **     **** *  * *
HIV.1 MRVKEKYQHLWRWGWKWGTMLLGILMICSATEKLWVTVYYGVPVWKEATTTLFCASDAKAYDTEVHNVWATHACVPTDPNPQEVVLVNVTENFNMWKNDM 100

LAV.2 TEQAIEDVWHLFETSIKPCVKLTPLCVAMKCSSTESSTGNNTTSKSTSTTTTT-PTDQE-QEISEDTPCARADNCSGLGEEETINCQFNMTGLERDKKKQ 177
       **  **   *   * ***********  **          ** *   *  *          *  **              ***        *
HIV.1 VEQMHEDIISLWDQSLKPCVKLTPLCVSLKCTDL----GNATNTNSSNTNSSSGEMMMEKGEIK---------NCSFNISTSIRGKVQKEYAFFYKLDII 187

LAV.2 Y--NET-WYSKDVVCETNNSTNQTQCYMNHCNTSVITESCDKHYWDAIRFRYCAPPGYALLRCNDT--NYSGFAPNCSKVVASTCTRMMETQTSTWF-GF 271
         * *  *                            *******  * *     *    **** * * * **    *  *    *  *   **      **
HIV.1 PIDNDTTSYTL-----------------TSCNTSVITQACPKVSFEPIPIHYCAPAGFAILKCNNKTFNGTGP---CTNVSTVQCTHGIRPVVSTQLLL- 266

LAV.2 NGTRAEN----RTYIYWHGRDN-RTII-SLNKYYNLSLHCKRPGNKTVKQIMLMS--GHVFHSHYQPINKRPRQAWCWFKG-KWKDAMQEVKETLAKHPR 362
       **  **      *        **  ***  **        * ** * * * * *    *  *       *  *** *    **        *    *
HIV.1 NGSLAEEEVVIRSANFT---DNAKTIIVQLNQSVE--INCTRPNNNTRKSIRIQRGPGRAFVTIGKIGN--MRQAHCNISRAKWNAT---LKQIASKLRE 356

LAV.2 YRGTNDTRNISFAAPGKGSDPEVAYMWTNCRGEFLYCNMTWFLN--WI----------ENKTHRNYAPCHIKQIINTWHKVGRNVYLPPREGELSCNST 449
         * *    * *    * ***     ** *** *** *    *  *               *        * *** ** *   **    * **  *    * *
HIV.1 QFGNN--KTIIFKQSS-GGDPEIVTHSFNCGGEFFYCNSTQLFNSTWFNSTWSTEGSNNTEGSDTITLPCRIKQFINMWQEVGKAMYAPPISGQIRCSSN 453

LAV.2 VTSIIANIDWQNNNQTNITFSAEVAELYRL---ELGDYKLVEITPIGFAPTKEKRYSSAHGRHTRGVFVLGFL--GFLATAGSAMGAAS--LTVSAQSRT 542
        *     *  ***      *                **   ** * * * * * **** **           *   * *     * *   ***   *** *** *   *** *  *
HIV.1 ITGLLLTRDGGNNNNGSEIFRPGGGDMRDNWRSELYKYKVVKIEPLGVAPTKAKRR--VVQREKRAVGI-GALFLGFLGAAGSTMGARSMTLTVQA--RQ 548

LAV.2 LLAGIVQQQQQLLDVVKRQQELLRLTVWGTKNLQARVTAIEKYLQDQARLNSWGCAFRQVCHTTVPW----VNDSLAPDWDNMTWQEWEKQVRYLEANIS 638
       ** ******  **       ** ** ***** * ****   * * ** **   *   ***         * * ***      *  *    * **** **          *
HIV.1 LLSGIVQQQNNLLRAIEAQQHLLQLTVWGIKQLQARILAVERYLKDQQLLGIWGCSGKLICTTAVPWNASWSNKSLEQIWNNMTWMEWDREINNYTSLIH 648

LAV.2 KSLEQAQIQQEKNMYELQKLNSWDIFGNWFDLTSWVKYIQYGVLIIVAVIALRIVIYVVQMLSRLRKGYRPV-FSSPPGYIQQIHIHKDRGQPANEETEE 737
          *  * *****  **  *   *    ***  * *  **       *       ****  *        * * ** *  *               *    **     *  **
HIV.1 SLIEESQNQQEKNEQELLELDKWASLWNWFNITNWLWYIKIFIMIVGGLVGLRIVFAVLSIVNRVRQGYSPLSFQT--------HLPTPRGPDRPEGIEE 740

LAV.2 DGGSNGGDRYWPWPIAYIHFLIRQLIRLLT-----RLYSICRDLLSRSFLTLQLIYQNLRDWLRLRTA--FLQYGCEWIQEAFQ----AAARATRETL-- 824
       **     **           **     * *         *     ****             *      * * *       ***               * * *  *
HIV.1 EGGERDRDRSIRLVNGSLA-LIWDDLRSLCLFSYHRL----RDLLLIVTRIVELLG--RRGWEALKYWWNLLQYWSQELKNSAVSLLNATAIAVAEGTDR 833

LAV.2 -----AGACRGLWRVLERIGRGILAVPRRIRQGAEIALL       858
          ****               *  ******* *  **
HIV.1 VIEVVQGACRA-----------IRHIPRRIRQGLERILL       861
```

FIG. 2

```
                                       P-VQHVGGNYTHIPLSPRTLNAWVKLVEEKKFGAEVVPGFQALSEGCTPYDINQMLNCVGDHQAA 199
                                       * **   *   *   ********** **** *  ** * * ***** ** * * *** ** ****
                                       PIVQNIQGQMVHQAISPRTLNAWVKVVEEKAFSPEVIPMFSALSEGATPQDLNTMLNTVGGHQAA 197

LAV-2 MQTIREIINEEAAEWDVQHPIP-GPLPAGQLREPRGSDIAGTTSTVEEQIQWMFR-PQNPVPVGNIYRRWIQIGLQKCVRMYNPTNILDIKQGPKEPFQS 297
      **   * *********  **   **   ** **************  *** **   *  * *** ** ***  ** * **** ** **** *******
HIV-1 MQMLKETINEEAAEWDRVHPVHAGPIAPGQMREPRGSDIAGTTSTLQEQIGWMTNNP--PIPVGEIYKRWITLGLNKIVRMYSPTSILDIRQGPKEPFRD 295

LAV-2 YVDRFYKSLRAEQTDPAVKNWMTQTLLVQNANPDCKLVLKGLGMNPTLEEMLTACQGVGGPGQKARLMAEALKEVIGPAPIP
      ******* *****    ****** ************  ** **   ***** ********** ***  ***   *   * *
HIV-1 YVDRFYKTLRAEQASQEVKNWMTETLLVQNANPDCKTILKALGPAATLEEMMTACQGYGGPGHKARVAEAMSQVTNSATIM
```

SYNTHETIC HIV-2 GAG AND ENV OLIGOPEPTIDES REACTIVE WITH HIV-2 SPECIFIC ANTIBODIES

This application is a continuation of Ser. No. 08/037,506, filed Mar. 24, 1993, now abandoned, which is a continuation of Ser. No. 07/807,426 filed Dec. 31, 1991, now abandoned, which is a continuation of Ser. No. 07/622,299 filed Dec. 5, 1990, now abandoned, which is a continuation of Ser. No. 07/035,408 filed Apr. 7, 1987, now abandoned, which is a continuation-in-part of Ser. No. 07/003,764 filed Jan. 16, 1987, now U.S. Pat. No. 5,051,496 and a continuation-in-part of Ser. No. 07/013,477 filed Feb. 11, 1987 now U.S. Pat. No. 5,079,342, and a continuation-in-part of Ser. No. 07/030,403 filed Mar. 25, 1987, now abandoned.

1. FIELD OF INVENTION

A novel human retrovirus, designated lymphadenopathy virus, type 2 ("LAV-2"), has recently been isolated from patients with Acquired Immune Deficiency Syndrome (AIDS) from West Africa. Although this virus is related to HIV-1 (also known as LAV/HTLV-III), sera from patients infected with LAV-2 are repeatedly negative or react poorly in screening assays for antibodies to HIV-1. Due to the serious threat to public health posed by a new virus associated with AIDS which is not sufficiently detected with the presently available tests for HIV-1, there has arisen an immediate need for a new antibody screening test. Desirably the test would be able to distinguish between individuals with antibodies to HIV-1 versus LAV-2.

To develop an immunodiagnostic test to identify individuals previously exposed to LAV-2, it is necessary to have LAV-2 proteins and/or antibodies to such proteins. Because of the hazards to laboratory workers associated with growing LAV-2, as well as the technical difficulties and expense of large scale culture and purification of virus, there is considerable interest in developing alternative means for obtaining the viral proteins or their immunologic equivalents. In choosing alternatives, one must be concerned with the fact that the HIV family of retroviruses has been reported to be highly polymorphic, as well as the possibility that additional members of the HIV family may be discovered.

2. BRIEF DESCRIPTION OF THE BACKGROUND ART

The isolation and partial characterization of LAV-2 from two AIDS patients from West Africa was initially described in Clavel et al., *C.r. Acad. Sci.* (Paris), 302:485–488 (1986) and Clavel et al., *Science* 233:343 (1986). This virus is related to HIV-1, the causative agent of AIDS, by both its morphology and its biological properties, the latter including its T4+ lymphotropism and its cytopathic effect on T4 cell lines and lymphocytes. However, DNA hybridization studies suggest that there are regions of extensive homology between HIV-1 and LAV-2 particularly in the gag gene, the reverse transcriptase domain in pol, the Q genes, the F gene, and the 3' LTR. The envelope gene, the tat gene, and part of the pol gene seem very divergent. Clavel et al. (ibid.)

Thus, even though HIV-1 and LAV-2 may be related, the heterogeneity in the genes which encode the envelope proteins may explain why serological cross-reactivity between the two species appears to be limited to epitopes of the gag and pol proteins. This may also account for the difficulties of the commercially available HIV-1 screening tests to adequately detect antibodies to LAV-2. Clavel et al. (ibid.) have predicted that, despite the wide divergence between the env genes of HIV-1 and LAV-2, there may exist homologous domains in the envelope glycoproteins of the two viruses which bind them to T4 receptors on the target cells.

It appears that LAV-2 may also be related to a virus known as Simian T-lymphotropic Virus Type 3 ("STLV-3"), a retrovirus first isolated from captive macaques with an AIDS-like disease. Clavel et al. (*Nature* 324:691–695 (1986)) used radioimmunoprecipitation assays to show that sera from patients infected with LAV-2 reacted with all the STLV-3 proteins, although the proteins of LAV-2 and STLV-3 were distinguishable by differences in molecular weights. The nucleotide sequence of LAV-2 may also be very similar to STLV-3, as LAV-2 probes bound STLV-3 gag and pol regions under stringent conditions, whereas HIV-1 probes did not react with the STLV-3 genome. Southern blots of STLV-3 DNA showed a restriction pattern that was clearly different, however, from LAV-2 DNA.

Another human retrovirus, designated HTLV-IV, has also been isolated from West African patients but has not been associated with an AIDS-like disease. This virus also appears related to STLV-3 and HIV-1 (Kanki et al., *Science* (1986) 232:238–243). Comparisons of HTLV-IV and LAV-2 have not been reported. Serological evidence for another new retrovirus related to STLV-3 has been reported in residents of West Africa. Barin et al., *Lancet,* 2:1387–89 (1985).

Hopp and Woods, *Proc. Nat. Acad. Sci. USA* (1981) 78:3824, describe criteria for selecting peptides as potential epitopes of polypeptides based on their relative hydrophilicity. In one study employing these criteria, a 12-amino acid peptide was synthesized that bound 9% of antibodies elicited by the native protein (Hopp, *Molec Immunol.* (1981) 18:869). In general Hopp/Woods criteria have not been shown to have a high predictive value, particularly for those regions not associated with the highest peak of hydrophilicity for a particular protein. Furthermore, epitopes have been demonstrated which are not hydrophilic (Kazim et al., *Biochem. J.* (1982) 203:201). Other studies of polypeptide antigenicity include Green et al., *Cell* (1982) 28:477, where peptides were employed which elicited antibodies, which antibodies were capable of binding to the native protein, while conversely antibodies which were elicited by the native protein failed to bind to the peptides; and Trainer et al., *Nature* (1984) 312:127, whose results with myohaemerythrin paralleled those of Green et al.

Synthetic peptides have been generated which immunologically mimic or have been predicted to mimic proteins encoded by HIV-1. See U.S. Pat. No. 4,629,783 and Pat. Publication No. WO 86/06414, which are incorporated herein by reference; NTIS Publication No. PB 86-131562 (U.S. patent application Ser. No. 779,431) and Chang et al., *Proc. Natl. Acad. Sci. USA* 83:6159–63 (1986). Pauletti et al., *Analyt. Biochem.* 151:540–546 (1985) used a computer program to predict possible antigenic determinants for the envelope glycoprotein (gp160) of HIV-1. Starcich et al., *Cell* 45:637–648 (1986) analyzed the entire envelope gene of isolates of HIV-1 and, based on predicted secondary protein structure and hydrophilicity, postulated that certain hypervariable regions represented antigenic sites.

3. SUMMARY OF THE INVENTION

Peptide sequences capable of immunologically mimicking proteins encoded in the env and gag regions of the LAV-2 retrovirus are provided as reagents for use in the screening of blood and blood products for prior exposure to the retrovirus. The peptides are at least five amino acids in length and can be used in various specific binding assays for the detection of antibodies to LAV-2 virus, for the detection of LAV-2 antigens, or as immunogens. Peptides described in the examples enable one to distinguish the presence of antibodies in a body fluid to LAV-2 from antibodies to HIV-1.

One peptide (41-2-1) described herein has the following amino acid sequence:

$Y_n$-Arg-Val-Thr-Ala-Ile-Glu-Lys-Tyr-Leu-Gln-Asp-Gln-Ala-Arg-Leu-Asn-Ser-Trp-Gly-Cys-Ala-Phe-Arg-Gln-Val-Cys-$Y'_{n'}$.

in which

Y and Y' each comprises one or more amino acid residues; and n and n' each comprises an integer of at least 0.

Another peptide (41-2-2) described herein has the following amino acid sequence:

$Y_n$-Ser-Lys-Ser-Leu-Glu-Gln-Ala-Gln-Ile-Gln-Gln-Glu-Lys-Asn-Nor-Tyr-Glu-Leu-Gln-Lys-Leu-Asn-Ser-Trp-Asp-$Y'_{n'}$.

in which Y and Y' each comprises one or more amino acid residues, and n and n' each comprises an integer of at least 0.

Another peptide (25-2-2) from the gag region described herein has the following amino acid sequence:

$Y_n$-Asp-Cys-Lys-Leu-Val-Leu-Lys-Gly-Leu-Gly-Nor-Asn-Pro-Thr-Leu-Glu-Gln-Nor-Leu-Thr-Ala-Cys-$Y'_{n'}$.

in which Y and Y', each represents one or more amino acid residues; and n and n' each are integers of at least 0.

3.1. DEFINITIONS

As used herein, "nor" is meant to refer to norleucine and is intended as a substitution for certain methionine residues.

As used herein, HIV is meant to refer to a human immunodeficiency virus characterized as a human retrovirus which is tropic for cells expressing the CD4 antigen and cytopathic to the host cell which it infects. This group includes but is not limited to HIV-1 (LAV-1/HTLV-III), and LAV-2.

4. BRIEF DESCRIPTION OF THE FIGURES

FIG. 1 represents the deduced amino acid sequences of the envelope region (including the transmembrane protein) of HIV-1 and LAV-2, using the one-letter symbols for amino acid residues as follows:

A (alanine), R (arginine), N (asparagine), D (aspartic acid), C (cysteine), Q (glutamine), E (glutamic acid), G (glycine), H (histidine), I (isoleucine), L (leucine), K (lysine), M (methionine), F (phenylalanine, P (proline), S (serine), T (threonine), W (tryptophan), Y (tyrosine), V (valine).

FIG. 2 represents the deduced amino acid sequences of the core (gag) region of HIV-1 and LAV-2, using the single letter symbols for amino acid residues as described for FIG. 1.

The sequences of the viruses are aligned to indicate maximum homologies between the two sequences.

5. DESCRIPTION OF THE SPECIFIC EMBODIMENTS

Novel peptides are provided which immunologically mimic proteins encoded by the LAV-2 retrovirus, particularly proteins encoded by the env and gag regions of the viral genome. To accommodate strain-to-strain variations among different isolates, adjustments for conservative substitutions, and selection among the alternatives where non-conservative substitutions are involved, may be made. These peptides can be used for the detection of the virus or of antibodies to the virus in a physiological sample. Depending upon the nature of the test protocol, the peptides may be labeled or unlabeled, bound to a solid surface, conjugated to a carrier or other compounds, or the like.

The peptides of interest will be derived from the envelope region of the virus. These peptides may be derived from a region of the envelope that is believed to be the transmembrane protein analogous to gp41 in HIV-1. Of particular interest is the region within the env open reading frame (see FIG. 1) extending from about amino acid residue numbers 556 to about 675, and, more particularly amino acid residue numbers 578 to 603, 578 to 598, or 578 to 591 of the open reading frame and from 587 to 603 or 590 to 603. Also of interest is the region extending from about amino acid residue 638 to about 662.

The peptides of interest may also be derived from the core region of the virus. Of particular interest are the regions within the gag open reading frame (see FIG. 2) extending from about amino acid residue numbers 331 to 352 and amino acid residue numbers 274 to 316 of the open reading frame.

The peptides of interest will include at least 5, sometimes 6, sometimes 8, sometimes 12, sometimes 14, sometimes 17, sometimes 21, usually fewer than about 50, more usually fewer than about 35, and preferably fewer than about 26 amino acids included within a sequence coded for by the LAV-2 retrovirus. Desirably, the peptide will be as small as possible while still maintaining substantially all of the sensitivity of the larger peptide. In some instances it may be desirable to join two or more oligopeptides which are non-overlapping to form a single peptide structure or to use them as individual peptides at the same time, which separately or together provide equivalent sensitivity to the parent.

The peptide may be modified by introducing conservative or non-conservative substitutions in the peptide, usually fewer than 20 number percent, more usually fewer than 10 number percent of the amino acids being exchanged. In those situations where regions are found to be polymorphic, it may be desirable to vary one or more particular amino acids to more effectively mimic the differing epitopes of the different retroviral strains. In many instances to provide chemical stability, methionine may be replaced by norleucine (Nor).

It should be understood that the polypeptide employed in the subject invention need not be identical to any particular LAV-2 polypeptide sequence, so long as the subject compound is able to immunologically mimic an epitope of at least one of the strains of the LAV-2 retrovirus. Therefore, the subject polypeptide may be subject to various changes, such as insertions, deletions, and substitutions, either conservative or non-conservative, where such changes might provide for certain advantages in their use. By conservative substitutions is intended substitutions within groups such as gly, ala; val, ile, leu; asp, glu; asn, gln; ser, thr; lys, arg; phe, tyr; and nor, met. Usually, the sequence will not differ by more than 20% from the sequence of at least one strain of an LAV-2 retrovirus except where additional amino acids may be added at either terminus for the purpose of providing an "arm" by which the peptide of this invention may be conveniently immobilized. The arms will usually be at least 1 amino acid and may be 50 or more amino acids, more often 1 to 10 amino acids, in length. The peptide in which the amino acid sequence is modified by the substitution, addition or deletion of amino acid residues should retain substantially all of the immunological reactivity of the unmodified peptides, which may be conveniently measured by radioimmuno-precipitation, immunofluorescence, or enzyme-linked immunosorbant assays.

In addition, one or two amino acids may be added to the termini of an oligopeptide or peptide to provide for ease of linking peptides one to another, for coupling to a support or larger peptide, for reasons to be discussed subsequently, for modifying the physical or chemical properties of the peptide or oligopeptide, or the like.

Amino acids such as tyrosine, cysteine, lysine, glutamic or aspartic acid, or the like, may be introduced at the C- or N-terminus of the peptide or oligopeptide to provide for a useful functionality for linking. Cysteine is particularly preferred to facilitate covalent coupling to other peptides or to form polymers by oxidation. To form polymers, it is preferred to have at least two cysteine residues present in the molecules being linked, preferably by utilizing cysteine residues added to the terminal portions of the peptides. Combinations of cysteine with intervening amino acid spacers are also useful. For example, two cysteine residues can be separated by one or more amino acid residues. Glycine residues are particularly useful and from one to three glycine residues may be employed between amino acids.

In addition, the peptide or oligopeptide sequences may differ from the natural sequence by the sequence being modified by terminal- $NH_2$ acylation, e.g., acetylation, or thioglycolic acid amidation, terminal-carboxy amidation, e.g., with ammonia or methylamine, to provide stability, increased hydrophobicity for linking or binding to a support or other molecule, or for polymerization.

The present invention is based, in part, upon the discovery that the amino acid sequence of peptides which immunologically mimic proteins of LAV-2 may be identified based upon their location within an LAV-2 protein. Such locations within LAV-2 proteins may be identified by reference to HIV-1 sequence data as follows:

(a) the amino acid sequences of HIV-1 and LAV-2 may be aligned to obtain maximum homology between the two sequences (see FIG. 1);

(b) Peptides comprising LAV-2 amino acid sequences that correspond to the location of HIV-1 peptides that immunologically mimic HIV-1 proteins may be identified. Despite the lack of extensive homology between such HIV-1 and LAV-2 sequences, peptides comprising LAV-2 amino acid sequences so identified should immunologically mimic LAV-2 proteins.

The method for identifying LAV-2 amino acid sequences that immunologically mimic a LAV-2 protein is demonstrated by the identification of peptides 41-2-1, 41-2-2, and 25-2-2 described in the examples herein. The sequence of peptide 41-2-1, 41-2-2, and 25-2-2 were discovered by aligning the envelope and core amino acid sequences of HIV-1 and LAV-2 to obtain maximum homologies. The LAV-2 amino acid sequences corresponding to the location of peptide 39 of HIV-1 was synthesized (peptide 39 of HIV-1 immunologically mimics the HIV-1 envelope; see U.S. Pat. No. 4,629,783). Similarly the LAV-2 amino acid sequence corresponding to the location of peptide 23 of HIV-1 (see U.S. Pat. No. 4,629,783) was synthesized. Additionally, the LAV-2 amino acid sequence corresponding to the location of peptide 15 of HIV-1 (see U.S. Pat. No. 4,629,783) was synthesized. The corresponding LAV-2 peptides, called 41-2-1, 41-2-2 and 25-2-2, respectively, as demonstrated in the examples herein, immunologically mimic LAV-2 and can be used to detect antibodies in body fluids. This method can similarly be applied to HIV strains that are yet to be discovered. For example, as new strains of HIV are identified their envelope and core amino acid sequences may be aligned with that of HIV-1 and/or LAV-2 to obtain maximum homology. The methods by which the sequences are aligned are known to those skilled in the art. In aligning the sequences it is desirable to maintain as much homology between cysteine residues as possible. The amino acid sequence of the new HIV strain or species which corresponds to the location of peptide 39 of HIV-1 or peptide 41-2-1 of LAV-2 can be synthesized and used in acccordance with the invention. Likewise, the amino acid sequence which corresponds to peptide 23 of HIV-1, as disclosed in U.S. Pat. No. 4,629,783, and peptide 41-2-2 of LAV-2 may be similarly identified and synthesized. Similarly, the amino acid sequence which corresponds to peptide 15 of HIV-1, as disclosed in U.S. Pat. No. 4,629,783, and peptide 25-2-2 of LAV-2 may be identified and synthesized.

Although the above-described method identifies amino acid sequences from regions of immunodominance, it is not necessary to the present invention that the epitopes contained within such sequences be cross-reactive with antibodies to all strains or species of HIV. Peptides encompassing immunological epitopes which distinguish one species or serogroup over another will find utility in identifying particular species or serogroups, and may in fact assist in identifying individuals infected with one or more species or serogroups of HIV.

A number of peptides of interest, derived from the envelope region of LAV-2 particularly the glycoprotein referred to as the transmembrane protein analogous to gp 41 of HIV-1, are described below. Peptide I, also designated 41-2-1, is encoded in the env open reading frame from about amino acid residue numbers 578 to about 603 and will have the following amino acid sequence, where oligopeptides included within the following sequence will include linear epitopes within such sequence:

(I) 41-2-1

$Y_n$-Arg-Val-Thr-Ala-Ile-Glu-Lys-Tyr-Leu-Gln-Asp-Gln-Ala-Arg-Leu-Asn-Ser-Trp-Gly-Cys-Ala-Phe-Arg-Gln-Val-Cys-$Y'_{n'}$.

in which Y and Y', when present, each represents one or more amino acid residues; and n and n' each comprises an integer of at least 0. When Y and/or Y' are present, these may comprise amino acid sequences which flank amino acid residues 578 through 603 of the LAV-2 envelope sequence (see FIG. 1), or any portion of these flanking sequences. In particular, Y can comprise all or portions of the LAV-2 envelope amino acid sequence from about residue numbers 556 to 577; Y' can comprise all or portions of LAV-2 envelope amino acid sequence from about residue numbers 604 to 675.

Alternatively, truncated sequences of peptide 41-2-1 may be prepared. In this regard, the following sequences may be particularly useful:

(II) 41-2-1(a)

$Y_n$-Arg-Val-Thr-Ala-Ile-Glu-Lys-Tyr-Leu-Gln-Asp-Gln-Ala-Arg-Leu-Asn-Ser-Trp-Gly-Cys-Ala-$Y'_{n'}$.

in which Y and/or Y', when present, each represents one or more amino acid residues; and n and n' each are integers of at least 0.

(III) 41-2-1 (b)

$Y_n$-Arg-Val-Thr-Ala-Ile-Glu-Lys Tyr-Leu-Gln-Asp-Gln-Ala-Arg-$Y'_{n'}$.

in which Y and Y', when present, each represents one or more amino acid residues; and n and n' each are integers of at least 0.

(IV) 41-2-3

$Y_n$-Gln-Asp-Gln-Ala-Arg-Leu-Asn-Ser-Trp-Gly-Cys-Ala-Phe-Arg-Gln-Val-Cys-$Y'_{n'}$.

in which Y and Y', when present, each represents one or more amino acid residues; and n and n' each are integers of at least 0.

(V) 41-2-4

$Y_n$-Ala-Arg-Leu-Asn-Ser-Trp-Gly-Cys-Ala-Phe-Arg-Gln-Val-Cys-$Y'_{n'}$ in which Y and Y', when present, each represents one or more amino acid residues; and n and n' each are integers of at least 0.

Another peptide of interest, also derived from the envelope region of LAV-2 and designated 41-2-2, or Peptide VI, comprises all or portions of the LAV-2 amino acid sequence from about residue number 638 to about 662 (FIG. 1), where oligo-peptides included within the following sequence will include linear epitopes within such sequence:

(VI) 41-2-2

$Y_n$-Ser-Lys-Ser-Leu-Glu-Gln-Ala-Gln-Ile-Gln-Gln-Glu-Lys-Asn-Met-Tyr-Glu-Leu-Gln-Lys-Leu-Asn-Ser-Trp-Asp-$Y'_{n'}$.

in which Y and Y' each comprises one or more amino acid residues, and n and n' each comprises an integer of at least 0.

Another peptide of interest, derived from the gag region of LAV-2 and designated 25-2-2, or Peptide VII, comprises all or portions of the LAV-2 amino acid sequence from about residue number 331 to 352 (FIG. 2), where ligopeptides included within the following sequence will include linear epitopes within such sequence:

(VII) 25-2-2

$Y_n$-Asp-Cys-Lys-Leu-Val-Leu-Lys-Gly-Leu-Gly-Nor-Asn-Pro-Thr-Leu-Glu-Glu-Nor-Leu-Thr-Ala-Cys-$Y'_{n'}$.

in which Y and Y', when present, each represents one or more amino acid residues; and n and n' each are integers of at least 0.

Another peptide of interest, also derived from the gag region of LAV-2 and designated 25-2-6, or Peptide VIII, comprises all or portions of the LAV-2 amino acid sequence from about residue number 274 to about 316, (FIG. 2), where oligopeptides included within the following sequence will include linear epitopes within such sequence:

(VIII) 25-2–6

$Y_n$-Lys-Cys-Val-Arg-Nor-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys-$Y'_{n'}$ in which Y and Y', when present, each represents one or more amino acid residues; and n and n' each are integers of at least 0.

When Y or Y' are present, a preferred embodiment exists when Y or Y' comprises one or more cysteine residues or a combination of one or more cysteine residues with spacer amino acids. Glycine is a particularly preferred spacer. Preferred peptides for use in oxidative polymerization are those in which Y or Y' represents at least two cysteine residues. When two cysteine residues are present at the same end of the peptide, a preferred embodiment exists when the cysteine residues are separated by from one to three spacer amino acid residues, preferably glycine. The presence of cysteine residues may allow the formation of dimers of the peptide and/or increase the hydrophobicity of the resulting peptide which facilitates immobilization of the peptide in solid phase or immobilized assay systems.

Of particular interest is the use of the mercaptan group of cysteines or thioglycolic acids used for acylating terminal amino groups or the like for linking two of the peptides or oligopeptides or combinations thereof by a disulfide linkage or a longer linkage. To achieve this, compounds may be employed having bis-haloacetyl groups, nitroarylhalides, or the like, where the reagents are specific for thio groups. Thus, the linking between the two mercapto groups of the different peptides or oligopeptides may be a single bond or a linking group of at least 2, usually at least 4, and not more than about 16, usually not more than about 14 carbon atoms.

The subject peptides may be employed linked to a soluble macromolecular (e.g., not less than 5 kDal) carrier. Conveniently, the carrier may be a poly(amino acid), either naturally occurring or synthetic, to which antibodies are unlikely to be encountered in human serum. Illustrative polypeptides include poly-L-lysine, bovine serum albumin, keyhole limpet hemocyanin, bovine gamma globulin, etc. The choice is primarily one of convenience and availability.

With such conjugates, there will be at least one molecule of at least one subject peptide per macromolecule and not more than about 1 per 0.5 kDal, usually not more than about 1 per 2 kDal of the macromolecule. One or more different peptides may be linked to the same macromolecule.

The manner of linking is conventional, employing such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The subject peptide may be derivatized by linking, may be linked while bound to a support, or the like.

The compounds may be employed as labeled or unlabeled compounds depending upon their use. (By label is intended a molecule which provides, directly or indirectly, a detectable signal.) Various labels may be employed, such as radionuclides, enzymes, fluorescers, chemiluminescers, enzyme substrates, cofactors or inhibitors,particles, e.g., magnetic particles, combinations of ligands and receptors, e.g., biotin and avidin, or the like. In addition, the polypeptides may be modified in a variety of ways for binding to a surface, e.g., microtiter plates, glass beads, chromatographic surface, e.g., paper, cellulose, silica gel, or the like. The particular manner in which the polypeptides are joined to another compound or surface is conventional and finds ample illustration in the literature. See, for example, U.S. Pat. Nos. 4,371,515; 4,487,715; and patents cited therein.

Various assay protocols may be employed for detecting the presence of either antibodies to retroviral proteins or retroviral proteins themselves. of particular interest is using the peptide as the labeled reagent, where the label allows for a detectable signal, or binding the peptide, either directly or indirectly to a surface, where antibody to the peptide in the sample will become bound to the peptide on the surface. The presence of human antibody bound to the peptide can then be detected by employing a xenogeneic antibody specific for human immunoglobulin, normally both human IgM and IgG, or a labeled protein specific for immune complexes, e.g., Rf factor or *S. aureus* protein A.

Various heterogeneous protocols may be employed, either competitive or non-competitive. Peptide may be bound to a surface or support ("support") and labeled antibody allowed to compete with antibody in the sample for the limited amount of bound peptide. The amount of label bound to the support would be related to the amount of competitive antibody in the sample.

Antibody could be bound to the support and the sample combined with labeled peptide. After contact of the reaction mixture with the bound antibody, the amount of label bound to the support would relate to the amount of cognate antibody in the sample.

Xenogeneic anti-human antibody, e.g., antibodies to the Fc of IgG and IgM (immunoglobulins), could be bound to a support. The sample would be contacted with the immunoglobulins and labeled peptide, whereby the amount of labeled peptide bound to the support would be indicative of the presence of the cognate antibodies.

Alternatively, homogeneous assays can be employed where the peptide is bound to an enzyme, fluorescer, or other label, where the binding of antibody to the peptide results in being able to discriminate between the label involved with a specific binding pair complex and label which is not involved in the complex. For assays involving such techniques, see for example U.S. Pat. Nos. 3,817,837; 3,850,752; 3,901,654; 3,935,074; 3,984,533; 3,996,345; 4,034,074; and 4,098,876, whose disclosures are incorporated herein by reference.

As an illustration of the subject invention the subject peptide may be conjugated to a fluorescent molecule, such as fluorescein, rhodamine or umbelliferone. Various techniques may be used for detecting complex formation with antibodies, e.g., fluorescence polarization. In this assay the fluorescence polarization is different between complexed and uncomplexed peptide conjugate. Apparatuses are available for measuring changes in fluorescence polarization, e.g., TDx supplied by Abbott Laboratories, Chicago, Ill.

Illustrative of an assay technique is the use of sample container, e.g., microtiter-plate wells, where the subject polypeptide or conjugates thereof are adhered to the container bottom and/or walls either covalently or non-covalently. The sample, normally human blood or serum diluted in appropriately buffered medium, is added to the container and a sufficient time allowed for complex formation between the polypeptide(s) and any cognate antibodies in the sample. The supernatant is removed and the container washed to remove nonspecifically bound proteins.

A labeled specific binding protein which specifically binds to the complex is employed for detection. To the container may be added xenogeneic antisera to human immunoglobulin, particularly anti-(human IgM and IgG) in an appropriately buffered medium. The xenogeneic antisera will normally be labeled with a detectable label, e.g., radionuclide or enzyme. Instead of antisera, proteins specific for the immune complex may be employed, e.g., *S aureus* protein A. The label may then be detected. For example, with an enzyme, after removal of non-specifically bound enzyme label, a developer solution is added. The developer solution will contain an enzyme substrate and possibly enzyme cofactors, chromogens, etc., which, upon reaction, provide a colored or fluorescent product which may be detected calorimetrically or fluorimetrically, respectively.

The peptide can be prepared in a wide variety of ways. The peptide, because of its relatively short size, may be synthesized in solution or on a solid support in accordance with conventional techniques. Various automatic synthesizers are commercially available today and can be used in accordance with known protocols. See, for example, Stewart and Young, Solid Phase Peptide Synthesis, 2nd ed., Pierce Chemical Co., 1984; and Tam et al., *J. Am. Chem. Soc.* (1983) 105:6442.

Alternatively, hybrid DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. See, for example, Maniatis et al., Molecular Cloning, A Laboratory Manual, CSH, Cold Spring Harbor Laboratory, 1982. Or, the region of the viral genome coding for the peptide may be cloned by conventional recombinant DNA techniques and expressed (see Maniatis, supra).

Fragments from a sequence may be employed for expression of peptide fragments, conservative base changes can be made, where the modified codon(s) code for the same amino acid(s), or non-conservative changes in the coding sequence may be made, where the resulting amino acid may be a conservative or non-conservative change in the amino acid sequence, which was discussed previously.

The coding sequence may be extended at either the 5'- or 3'-terminus or both termini to extend the peptide, while retaining its epitopic site(s). The extension may provide for an arm for linking, e.g., to a label, such as an enzyme, for joining this and other peptides together in the same chain, for providing antigenic activity, or the like.

For expression, the coding sequence will be provided with start and stop codons, promoter and terminator regions and usually a replication system to provide an expression vector for expression in a cellular host, e.g., prokaryotic or eukaryotic, bacterial, yeast, mammal, etc.

The DNA sequence by itself, fragments thereof, or larger sequences, usually at least 15 bases, preferably at least 18 bases, may be used as probes for detection of retroviral RNA or proviral DNA. Numerous techniques are described, such as the Grunstein-Hogness technique, Southern technique, Northern technique, dot-blot, improvements thereon, as well as other methodology. See, for example, WO 83/02277 and Berent et al., *Biotechniques* (1985) 3:208.

Conveniently, the polypeptide may be prepared as a fused protein, where the polypeptide may be the N- or C- terminus of the fused polypeptide. The resulting fused protein could be used directly by itself as the reagent or the subject polypeptide may be cleaved from all or a portion of the remaining sequence of the fused protein. With a polypeptide where there are no internal methionines, by introducing a methionine at the fusion site, the polypeptide may be cleaved employing cyanogen bromide. Where there is an internal methionine, it would be necessary to provide for a proteolytic cleavage site, e.g., polylysine and/or -arginine or combinations thereof, or the internal methionine could be substituted by an amino acid such as leucine and an N-terminal methionine added for cyanogen bromide cleavage. A wide variety of proteases, including dipeptidases, are well known, and the appropriate processing signal could be introduced at the proper site. The processing signal may have tandem repeats so as to insure cleavage, since the presence of one or more extraneous amino acids will not interfere with the utility of the subject polypeptides.

Depending upon the nature of the assay, the physiological sample, e.g., saliva, blood, plasma, or serum, may be pretreated by dilution into an assay medium, which will usually be an aqueous buffered medium employing one of a variety of buffers, such as phosphate, tris, or the like. A preferred diluent is 2.5% w/v nonfat dry milk, 0.01% thimerosal, 0.05% Antifoam A in 20 mM sodium citrate. Usually the pH will be in the range of about 6 to 9. The sample will then be combined with the reagent in accordance with the appropriate protocol and sufficient time allowed for binding. Where a heterogeneous system is used, usually the binding stages will be followed by washes to minimize non-specific binding. At the end of the procedure, the label will be detected in accordance with conventional methods.

Besides the use of the subject peptide and its analogs in assays, the subject peptide may also find use by itself or in combination in vaccines. The peptides may be formulated in a convenient manner, generally at concentrations in the range of 1 ug to 20 mg/kg of host. Physiologically acceptable media may be used as carriers, such as sterile water, saline, phosphate buffered saline, and the like. Adjuvants may be employed, such as aluminum hydroxide gel, or the like. Administration may be by injection, e.g., intramuscularly, peritoneally, subcutaneously, intravenously, etc. Administration may be one or a plurality of times, usually at one to four week intervals.

The following examples are offered by way of illustration and not by way of limitation.

6. EXPERIMENTAL

Peptides I (41-2-1), IV (41-2-3), V (41-2-4) and VII (25-2-2) were assembled on a t-butyloxycarbonyl (BOC)-methylbenzylcysteine-phenyl-acetamidomethyl (PAM) polystyrene/divinylbenzene resin (Applied Biosystems, Inc., Foster City, Calif.). Symmetrical anhydride couplings were carried out in an Applied Biosystems 430A synthesizer.

Peptide II (41-2-2) was assembled on a t-butyloxycarbonyl (BOC)- methylbenzylaspartic-phenyl-acetamidomethyl (PAM) polystyrene/divinylbenzene resin (Applied Biosystems, Inc., Foster City, Calif.). Symmetrical anhydride couplings were carried out in an Applied Biosystems 430A synthesizer.

Peptide VIII (25-2-6) was assembled on a t-butyloxycarbonyl (BOC)- chlorobenzyloxycarbonyl lysine-phenyl-acetamidomethyl (PAM) polystyrene/divinylbenzene resin (Applied Biosystems, Inc., Foster City, Calif.). Symmetrical anhydride couplings were carried out in an Applied Biosystems 430A synthesizer.

Dicyclohexycarbodiimide couplings in the presence of hydroxybenzotriazole were used for asparagine and glutamine. Benzyl-based side chain protection and BOC alpha-amine protection were used. Other side chain protection routinely used was BOC (formyl) tryptophan, BOC methionine sulfoxide, BOC (tosyl) arginine, BOC (methylbenzyl) cysteine, BOC (tosyl) histidine, BOC (chlorobenzyloxycarbonyl) lysine and BOC (bromobenzyloxycarbonyl) tyrosine.

Deprotection and cleavage of the peptide from the resin was by the Tam "low-high" HF protocol (Tam et al., supra). Extraction from the resin was with 5% acetic acid and the extract was subjected to gel filtration chromatography in 5% acetic acid.

Peptide 39 was prepared as described in U.S. Pat. No. 4,629,783, which is incorporated herein by reference.

6.1. Analysis by Elisa

Peptides 41-2-1 and 39 were stored as stock solutions of 4 mg/ml in 6 M Guanidine-HCl or as the oxidized peptide stocks described above. The peptides were diluted in 0.05 M sodium carbonate/bicarbonate buffer (pH 9.3) to final concentrations of 6.25 ug/ml (peptide 41-2-1) and 20 ug/ml (peptide 39). One hundred microliter aliquots were added per microtiter well and incubated overnight at room temperature. Plates were then blocked with blotto (5% [w/v] nonfat dry milk, 0.01% thimerosal, 0.01% Antifoam A in 0.01 M sodium phosphate, pH 7.2, 0.15 M sodium chloride) containing 0.5 M ethanolamine for one hour at room temperature. Serum or plasma samples were diluted 1:101 with diluent (2.5% [w/v] nonfat dry milk, 0.01% thimerosal, 0.005% Antifoam A in 20 mM sodium citrate) and 100 ul of diluted serum or plasma was added per well for one hour at 37° C. The sera or plasma were aspirated, and the plates were washed three times in wash buffer (0.15 M NaCl, 0.05% [w/v] Tween 20) before adding 100 ul of the goat anti-human Ig/horseradish peroxidase conjugate (diluted 1:10,000 in diluent containing 1% normal goat serum in citrate buffer, pH 7.0) for one hour at 37° C. The conjugate was removed, and the plates were again washed three times as described above. The ELISA assay was developed by adding 100 ul/well of substrate solution (80 ug/ml tetramethyl-benzidine, 0.0015% hydrogen peroxide in citrate/phosphate buffer, pH 6.0) for thirty minutes at room temperature. Reactions were stopped with the addition of 100 ul of 3N $H_2SO_4$ per well, and the ratio of the optical density at 450 nm to 630 nm was determined by an automated ELISA reader.

Peptide 41-2-2 was prepared as described above, but diluted to a final concentration of 1.6 ug/ml before adding 100 ul aliquots to the wells. Peptides 41-2-3, 41-2-4, 25-2-2, and 25-2-6 were prepared to final concentrations of 3.1 ug/ml, 12.5 ug/ml, 50 ug/ml, and 12.5 ug/ml, respectively, before adding 100 ul aliquots to wells. The sera or plasma for assays with 41-2-2, 41-2-3, 41-2-4, 25-2-2 and 25-2-6 were diluted 1:41 as described above, then incubated for 30 minutes at 37° C. after being added to the wells. All other conditions and reagents were as described above, with the exception that the incubation with the conjugate was at 37° C. for 30 minutes, and the incubation with the substrate was at room temperature for 30 minutes.

ELISAs using disrupted HIV-1 were carried out on commercially available LAV-EIA plates (Genetic Systems, Seattle, Wash.) using the LAV-1 isolate grown in CEM. ELISAs using disrupted LAV-2 coated on microwell plates were similarly prepared using the ROD isolate of LAV-2. The assays were performed essentially as described above.

6.2. ANALYSIS BY WESTERN IMMUNOBLOT AND RADIOIMMUNOPRECIPITATION ASSAY

Test sera were analyzed by Western immunoblot and radioimmunoprecipitation for the presence of antibodies to specific proteins and glycoproteins of HIV-1 and LAV-2. For immunoblotting, viral extracts were prepared from CEM cells infected with HIV-1 (LAV-1 isolate) or LAV-2 (ROD isolate) adapted to lytic growth. Virus was purified from cell culture supernatants using tangential flow filtration and sucrose gradient centrifugation. The concentrated virus was then disrupted in SDS-PAGE sample buffer and the proteins were separated by polyacrylamide gradient gel electrophoresis (7.0–15.0%) and transferred to nitrocellulose membrane (NCM) by electrophoresis for four hours at 25 V in 25 mM sodium phosphate (pH7.0). After transfer, the NCM was blocked to prevent nonspecific interactions by incubation in blotto for one hour at room temperature. The NCM was incubated with serum diluted 1:100 in blotto overnight at room temperature and was rinsed with three changes of PBS-Tween. In the second step the NCM was incubated with anti-human IgG-horseradish peroxidase diluted 1:10,000 in blotto for one hour at room temperature. This incubation was followed by washing with PBS-Tween and then immersion in horseradish peroxidase color development solution (0.5 mg/ml 4-chloro 1-napthol, 0.015% $H_2O_2$ in tris-buffered saline) for 20 minutes. The reaction was stopped by immersion in deionized water.

To prepare viral extracts for radioimmunoprecipitation, when infected CEM cell cultures reached a reverse transcriptase activity level of greater than $1\times10^6$cpm/ml the cells were transferred to labeling media containing $^{35}$S-methionine (0.05 mCi/ml) or $^3$H-glucosamine (0.025 mCi/ml), then incubated for 24 h. Virus was purified from cell culture supernatants (100,000×g) and detergent extracts prepared using P-RIPA buffer (PBS containing 1.0% Triton x-100, 1.0% deoxycholate, 0.1% sodium dodecyl sulfate, and 1% Aprotinin). Similar extracts were prepared from uninfected CEM cells. Immunoprecipitation assays were performed with 100 ul of virus extract incubated with 5 ul serum for one hour on ice. Immunoprecipitin (100 ul, BRL, Bethesda, Md.) resuspended in P-RIPA buffer containing 1.0% ovalbumin was added to each sample and incubated for an additional 30 minutes. The bound complexes were washed and separated by SDS-polyacrylamide gel electrophoresis (15% acrylamide DATD gels prepared at a ratio of 30% acrylamide to 1.2% DATD). Following electrophoresis the gels were fixed, soaked in EnHance (New England Nuclear, Boston, Mass.), dried and exposed to Kodak EX-5 film.

The criteria for positive in Western blots and RIPs was the presence of antibodies to at least one of the envelope glycoproteins: gp110 and gp41 for HIV-1 and gp140 for LAV-2 with or without antibodies to the core proteins p18 and p25 for HIV-1 and p16 and p26 for LAV-2. Sera with bands to internal proteins only were not considered true positives. See Rey et al., *Lancet* 2:1391–1392 (1986).

Results of the serum and plasma screen with peptides 41-2-1 and 41-2-2 are presented in Table I and are summarized as follows: Of the 22 samples positive for antibodies to LAV-2 as determined by either immunoblot or radioimmunoprecipitation, ELISAs using LAV-2 viral lysates detected 21 as positive, peptide 41-2-1 detected 19 as positive, and peptide 39 (HIV-1) detected none. Of the nine samples tested with peptide 41-2-2, all were correctly identified. The specificity of peptides 41-2-1 and 41-2-2 for antibodies to LAV-2 is demonstrated by their lack of reactivity with antibodies to HIV-1. Peptides 41-2-1 and 41-2-2 did not react with any of the 16 samples confirmed positive for antibodies to HIV-1 by Western blot whereas peptide 39 (HIV-1 specific) detected all as positive.

Results of the serum and plasma screen with peptides 41-2-3, 41-2-4, 25-2-2 and 25-2-6 are shown in Table II. Of the ten samples containing antibodies to LAV-2 and tested by peptides 41-2-3 and 41-2-4 all were detected as positive, and neither peptide cross-reacted with samples containing antibodies to HIV-1. Gag peptides 25-2-2 and 25-2-6 were tested against a limited number of LAV-2 positive sera, but detected all as positive. One HIV-1 positive sample was reactive with peptide 25-2-2.

The present invention has been described in detail with particular reference to the above embodiments. It will be understood, however, that the present invention is not to be limited in scope by the embodiments disclosed which are intended as illustrations of aspects of the invention.

TABLE I

COMPARISON OF PEPTIDES 41-2-1, 41-2-2, AND 39 WITH LAV-2 LYSATE FOR DETECTION OF ANTIBODIES TO LAV-2

| Serum No. | ELISA LAV-2 Lysate | ELISA Peptide 41-2-1 | ELISA Peptide 39 | ELISA Peptide 41-2-2 | Western blot HIV-1 | Western blot LAV-2 |
|---|---|---|---|---|---|---|
| 5518 | 1.166 | 2.340 | 0.072 | N.D.[1] | − | + |
| 5553 | 0.984 | 2.400 | 0.124 | 2.287 | − | + |
| 5554 | 1.448 | 2.550 | 0.255 | 2.624 | − | + |
| 5556 | 1.113 | 2.390 | 0.228 | 2.504 | − | + |
| 5557 | 0.872 | 2.320 | 0.119 | 2.524 | − | + |
| 5558 | 1.368 | 2.510 | 0.208 | 2.625 | − | + |
| 5559 | 1.590 | 2.510 | 0.197 | 2.328 | − | + |
| 5629 | 1.009 | 2.380 | 0.097 | N.D. | − | + |
| LG272 | 1.245 | 2.420 | 0.107 | 2.518 | − | + |
| LG339 | 1.087 | 2.500 | 0.123 | N.D. | − | + |
| LG401 | 1.495 | 2.610 | 0.147 | N.D. | − | + |
| PIN | 0.946 | 2.570 | 0.080 | 2.569 | − | + |
| ROD | 1.482 | 2.490 | 0.243 | 2.439 | − | + |
| COR | 0.210 | 0.670 | 0.069 | N.D. | − | + |
| 1966 | 2.048 | 1.370 | 0.085 | N.D. | N.D.[2] | + |
| 2099 | 1.147 | 0.930 | 0.085 | N.D. | N.D.[2] | + |
| 2156 | 1.314 | 1.830 | 0.106 | N.D. | N.D.[2] | + |
| 2759 | 1.899 | 2.260 | 0.167 | N.D. | N.D.[2] | + |
| 2852 | 0.787 | 0.490 | 0.175 | N.D. | N.D.[2] | + |
| Bge 7 | 1.196 | 1.670 | 0.252 | N.D. | N.D.[2] | + |
| Bge 12 | 2.077 | 2.180 | 0.272 | N.D. | N.D.[2] | + |
| Bge 13 | 1.001 | 0.440 | 0.152 | N.D. | N.D.[2] | + |
| A | N.D. | 0.080 | 1.960 | 0.111 | + | N.D. |
| C | N.D. | 0.080 | 1.210 | 0.055 | + | N.D. |
| D | N.D. | 0.100 | 1.960 | 0.095 | + | N.D. |
| G | N.D. | 0.120 | 2.080 | 0.119 | + | N.D. |
| H | N.D. | 0.120 | 2.070 | 0.084 | + | N.D. |
| I | N.D. | 0.090 | 2.060 | 0.065 | + | N.D. |
| J | N.D. | 0.100 | 2.160 | 0.085 | + | N.D. |
| K | N.D. | 0.090 | 2.120 | 0.100 | + | N.D. |

TABLE I-continued

COMPARISON OF PEPTIDES 41-2-1, 41-2-2, AND 39 WITH LAV-2 LYSATE FOR DETECTION OF ANTIBODIES TO LAV-2

| Serum No. | ELISA LAV-2 Lysate | ELISA Peptide 41-2-1 | ELISA Peptide 39 | ELISA Peptide 41-2-2 | Western blot HIV-1 | Western blot LAV-2 |
|---|---|---|---|---|---|---|
| L | N.D. | 0.100 | 2.070 | 0.150 | + | N.D. |
| M | N.D. | 0.130 | 2.180 | 0.049 | + | N.D. |
| N | N.D. | 0.130 | 2.180 | 0.049 | + | N.D. |
| O | N.D. | 0.090 | 2.190 | 0.096 | + | N.D. |
| P | N.D. | 0.110 | 1.420 | 0.039 | + | N.D. |
| Q | N.D. | 0.080 | 0.733 | 0.039 | + | N.D. |
| R | N.D. | 0.100 | 1.523 | 0.063 | + | N.D. |
| S | N.D. | 0.140 | 1.378 | 0.123 | + | N.D. |
| NHS-1[3] | N.D. | 0.310 | 0.102 | 0.097[4] | N.D. | N.D. |
| NHS-2 | N.D. | 0.300 | 0.103 | N.D. | N.D. | N.D. |

[1]N.D. = Not Determined.
[2]This serum was negative for antibodies to HIV-1 as determined by radioimmunoprecipitation assay.
[3]NHS-1 and 2 are normal human sera which served as negative controls. The cutoff values in the ELISAs are calculated as the mean of the negative controls plus 0.225 O.D. units.
[4]This value is the mean of 13 normal human sera tested with peptide 41-2-2, although sera NHS-1 and -2 were not included in this group.

TABLE II

REACTIVITY OF PEPTIDES 41-2-3, 41-2-4, 25-2-2, AND 25-2-6 IN ELISAs FOR DETECTION OF ANTIBODIES TO LAV-2 OR HIV-1

| Serum No. | Antibody Status[1] | Peptide 41-2-3 | Peptide 41-2-4 | Peptide 25-2-2 | Peptide 25-2-6 |
|---|---|---|---|---|---|
| PIN | LAV-2+ | 2.440 | 1.984 | 2.183 | 1.255 |
| LG272 | LAV-2+ | 1.727 | 1.149 | 2.252 | N.D.[2] |
| 5558 | LAV-2+ | 1.919 | 1.609 | N.D. | N.D. |
| 5557 | LAV-2+ | 1.830 | 0.987 | N.D. | N.D. |
| 5556 | LAV-2+ | 1.822 | 0.876 | N.D. | N.D. |
| 5554 | LAV-2+ | 2.447 | 2.252 | N.D. | N.D. |
| LG401 | LAV-2+ | 2.149 | 2.202 | N.D. | N.D. |
| LG339 | LAV-2+ | 2.525 | 2.594 | N.D. | N.D. |
| 5629 | LAV-2+ | 2.466 | 2.526 | N.D. | N.D. |
| 5518 | LAV-2+ | 1.725 | 0.601 | N.D. | N.D. |
| 5533 | LAV-2+ | N.D. | N.D. | 1.911 | N.D. |
| A | HIV-1+ | 0.080 | 0.229 | 0.245 | 0.367 |
| C | HIV-1+ | 0.065 | 0.211 | 0.137 | N.D. |
| D | HIV-1+ | 0.054 | 0.171 | 0.069 | 0.108 |
| G | HIV-1+ | 0.070 | 0.185 | 1.251 | N.D. |
| H | HIV-1+ | 0.063 | 0.217 | 0.145 | 0.150 |
| I | HIV-1+ | 0.068 | 0.181 | 0.201 | 0.198 |
| J | HIV-1+ | 0.057 | 0.222 | 0.101 | 0.186 |
| K | HIV-1+ | 0.057 | 0.205 | 0.077 | N.D. |
| L | HIV-1+ | 0.067 | 0.221 | 0.128 | 0.335 |
| M | HIV-1+ | 0.057 | 0.223 | 0.162 | N.D. |
| N | HIV-1+ | 0.068 | 0.236 | 0.155 | N.D. |
| O | HIV-1+ | 0.062 | 0.235 | 0.160 | N.D. |
| P | HIV-1+ | 0.068 | 0.197 | 0.104 | N.D. |
| Q | HIV-1+ | 0.069 | 0.165 | 0.095 | N.D. |
| R | HIV-1+ | 0.072 | 0.250 | 0.141 | N.D. |
| S | HIV-1+ | 0.071 | 0.226 | 0.150 | N.D. |
| Cutoff[3] | | 0.288 | 0.416 | 0.399 | N.D. |

[1]Presence of antibodies to LAV-2 ("LAV-2+") or HIV-1 ("HIV-1+") was confirmed by Western blot or radioimmunoprecipitation, as shown in Table I.
[2]N.D. = Not Determined
[3]Cutoff values were calculated as the mean of at least eight negative control sera plus 0.225 O.D. units.

What is claimed is:

1. A peptide consisting of the following HIV-2 sequence:

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys, or an antigenic fragment of said peptide, wherein the peptide or antigenic fragment is immunologically reactive with antibodies to HIV-2.

2. A method for determining the presence of antibodies to HIV-2 in a physiological sample, comprising:

(a) contacting a specimen of said physiological sample, under conditions permitting antigen-antibody binding, with a peptide consisting of the following HIV-2 sequence:

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys, wherein the peptide or antigenic fragment is immunologically reactive with antibodies to HIV-2; and (b) detecting whether antigen-antibody binding has occurred between said peptide or antigenic fragment and an antibody component of the specimen, in which the detection of antigen-antibody binding indicates the presence of antibodies to HIV-2 in the physiological sample.

3. The method according to claim 3, whereby said antigen-antibody binding of step (b) is measured by immunoprecipitation, immunofluorescence, or enzyme-linked immunosorbent assay.

4. The method of claim 3 wherein said peptide is a first peptide, further comprising contacting a specimen of said physiological sample, under conditions permitting antigen-antibody binding, with a second peptide consisting of a peptide selected from one of the following HIV-2 sequences:

(I) 41-2-1

Arg-Val-Thr-Ala-Ile-Glu-Lys-Tyr-Leu-Gln-Asp-Gln-Ala-Arg-Leu-Asn-Ser-Trp-Gly-Cys-Ala-Phe-Arg-Gln-Val-Cys (IV) 41-2-3

Gln-Asp-Gln-Ala-Arg-Leu-Asn-Ser-Trp-Gly-Cys-Ala-Phe-Arg-Gln-Val-Cys (V) 41-2-4

Ala-Arg-Leu-Asn-Ser-Trp-Gly-Cys-Ala-Phe-Arg-Gln-Val-Cys (VI) 41-2-2

Ser-Lys-Ser-Leu-Glu-Gln-Ala-Gln-Ile-Gln-Gln-Glu-Lys-Asn-Met-Tyr-Glu-Leu-Gln-Lys-Leu-Asn-Ser-Trp-Asp (VII) 25-2-2

Asp-Cys-Lys-Leu-Val-Leu-Lys-Gly-Leu-Gly-Met-Asn-Pro-Thr-Leu-Glu-Glu-Met-Leu-Thr-Ala-Cys; or (VIII) 25-2-6

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys;

wherein the peptide or antigenic fragment thereof is immunoreactive with antibodies to HIV-2.

5. The method according to claim 2, in which the peptide or antigenic fragment is conjugated to a carrier molecule.

6. The method according to claim 2, in which the peptide or antigenic fragment is immobilized.

7. The method of claim 2, wherein the antigen-antibody binding between the peptide and an antibody component of the specimen is detected by:

(i) removing unbound components from reaction products formed in the contacting step;

(ii) adding a labeled antibody to the reaction products of the contacting step, the labeled antibody being capable of antigen-antibody binding to a component of the reaction product and the label providing a detectable signal; and (iii) detecting whether the labeled antibody binds to the reaction products.

8. The method of claim 7, wherein the label comprises an enzyme which is detected by the addition of enzyme substrate.

9. The method of claim 7, wherein the label comprises a radiolabel or fluorescent label.

10. The peptide or antigenic fragment of claim 1, wherein the HIV-2 sequence is:

(VIII) 25-2-6

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys.

11. The method of claim 2, wherein the specimen is contacted with the peptide consisting of the HIV-2 sequence:

(VIII) 25-2-6

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys.

12. An antigen composition comprising a peptide consisting of the following HIV-2 sequence:

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys, or an antigenic fragment of said peptide, wherein the peptide or antigenic fragment is immunologically reactive with antibodies to HIV-2 and a second peptide or antigenic fragment consisting of a peptide selected from one of the following HIV-2 sequences:

(I) 41-2-1

Arg-Val-Thr-Ala-Ile-Glu-Lys-Tyr-Leu-Gln-Asp-Gln-Ala-Arg-Leu-Asn-Ser-Trp-Gly-Cys-Ala-Phe-Arg-Gln-Val-Cys (IV) 41-2-3

Gln-Asp-Gln-Ala-Arg-Leu-Asn-Ser-Trp-Gly-Cys-Ala-Phe-Arg-Gln-Val-Cys (V) 41-2-4

Ala-Arg-Leu-Asn-Ser-Trp-Gly-Cys-Ala-Phe-Arg-Gln-Val-Cys (VI) 41-2-2

Ser-Lys-Ser-Leu-Glu-Gln-Ala-Gln-Ile-Gln-Gln-Glu-Lys-Asn-Met-Tyr-Glu-Leu-Gln-Lys-Leu-Asn-Ser-Trp-Asp (VII) 25-2-2

Asp-Cys-Lys-Leu-Val-Leu-Lys-Gly-Leu-Gly-Met-Asn-Pro-Thr-Leu-Glu-Glu-Met-Leu-Thr-Ala-Cys; or (VIII) 25-2-6

Lys-Cys-Val-Arg-Met-Tyr-Asn-Pro-Thr-Asn-Ile-Leu-Asp-Ile-Lys-Gln-Gly-Pro-Lys-Glu-Pro-Phe-Gln-Ser-Tyr-Val-Asp-Arg-Phe-Tyr-Lys-Ser-Leu-Arg-Glu-Gln-Thr-Asp-Pro-Ala-Val-Lys;

wherein the peptide or antigenic fragment thereof is immunoreactive with antibodies to HIV-2.

* * * * *